(12) United States Patent
Liepold et al.

(10) Patent No.: US 9,402,909 B2
(45) Date of Patent: Aug. 2, 2016

(54) PHARMACEUTICAL DOSAGE FORM COMPRISING POLYMERIC CARRIER COMPOSITION

(71) Applicant: Abbvie Deutschland GmbH & Co. KG, Wiesbaden (DE)

(72) Inventors: Bernd Liepold, Dossenheim (DE); Jörg Breitenbach, Mannheim (DE); Markus Mägerlein, Mannheim (DE); Claudia Henzel, Mannheim (DE); Thomas K. Kessler, Schifferstadt (DE)

(73) Assignee: Abbvie Deutschland GmbH & Co KG, Wiesbaden (DE)

( * ) Notice: Subject to any disclaimer, the term of this patent is extended or adjusted under 35 U.S.C. 154(b) by 46 days.

(21) Appl. No.: 14/152,567

(22) Filed: Jan. 10, 2014

(65) Prior Publication Data

US 2014/0200278 A1    Jul. 17, 2014

Related U.S. Application Data

(63) Continuation of application No. 13/001,060, filed as application No. PCT/EP2009/058187 on Jun. 30, 2009, now abandoned.

(30) Foreign Application Priority Data

Jun. 30, 2008    (EP) ..................... 08159367

(51) Int. Cl.
*A61K 47/32*    (2006.01)
*A61K 9/20*    (2006.01)

(52) U.S. Cl.
CPC ............. *A61K 47/32* (2013.01); *A61K 9/2018* (2013.01); *A61K 9/2027* (2013.01); *A61K 9/2077* (2013.01); *A61K 9/2095* (2013.01)

(58) Field of Classification Search
CPC .... A61K 47/32; A61K 9/2027; A61K 9/2077
USPC ......................................... 424/489
See application file for complete search history.

(56) References Cited

U.S. PATENT DOCUMENTS 8,093,289 B2    1/2012 Kakuda et al.
2005/0245637 A1    11/2005 Hossainy et al.
(Continued)

FOREIGN PATENT DOCUMENTS

DE    19602206 A1    7/1997
DE    10249029 A1    4/2003
(Continued)

OTHER PUBLICATIONS

English translation of Notification of Rejection Issued in Japanese Application No. 2011-515431, dated Nov. 22, 2013.
(Continued)

*Primary Examiner* — Rachael E Bredefeld
(74) *Attorney, Agent, or Firm* — Saul Ewing LLP; Peter C. Lauro, Esq.

(57) ABSTRACT

A pharmaceutical dosage form comprises a solid dispersion product of at least one active ingredient dispersed in a polymeric binder composition, the polymeric carrier composition comprising a) a vinylpyrrolidone homopolymer, wherein at least 95% by weight of the vinylpyrrolidone homopolymer has a molecular weight distribution within the range of from 1000 to 13 000; and b) a vinylpyrrolidone copolymer having a weight-average molecular weight of from 5000 to 1 500 000. The dosage form is preferably prepared by a melt extrusion process. The polymeric carrier composition exhibits a high drug dissolution power and allows a reduction of the viscosity of the melt without deteriorating the mechanical properties and storage stability of the dosage form.

10 Claims, 5 Drawing Sheets

(56) References Cited

U.S. PATENT DOCUMENTS

Figure 1:
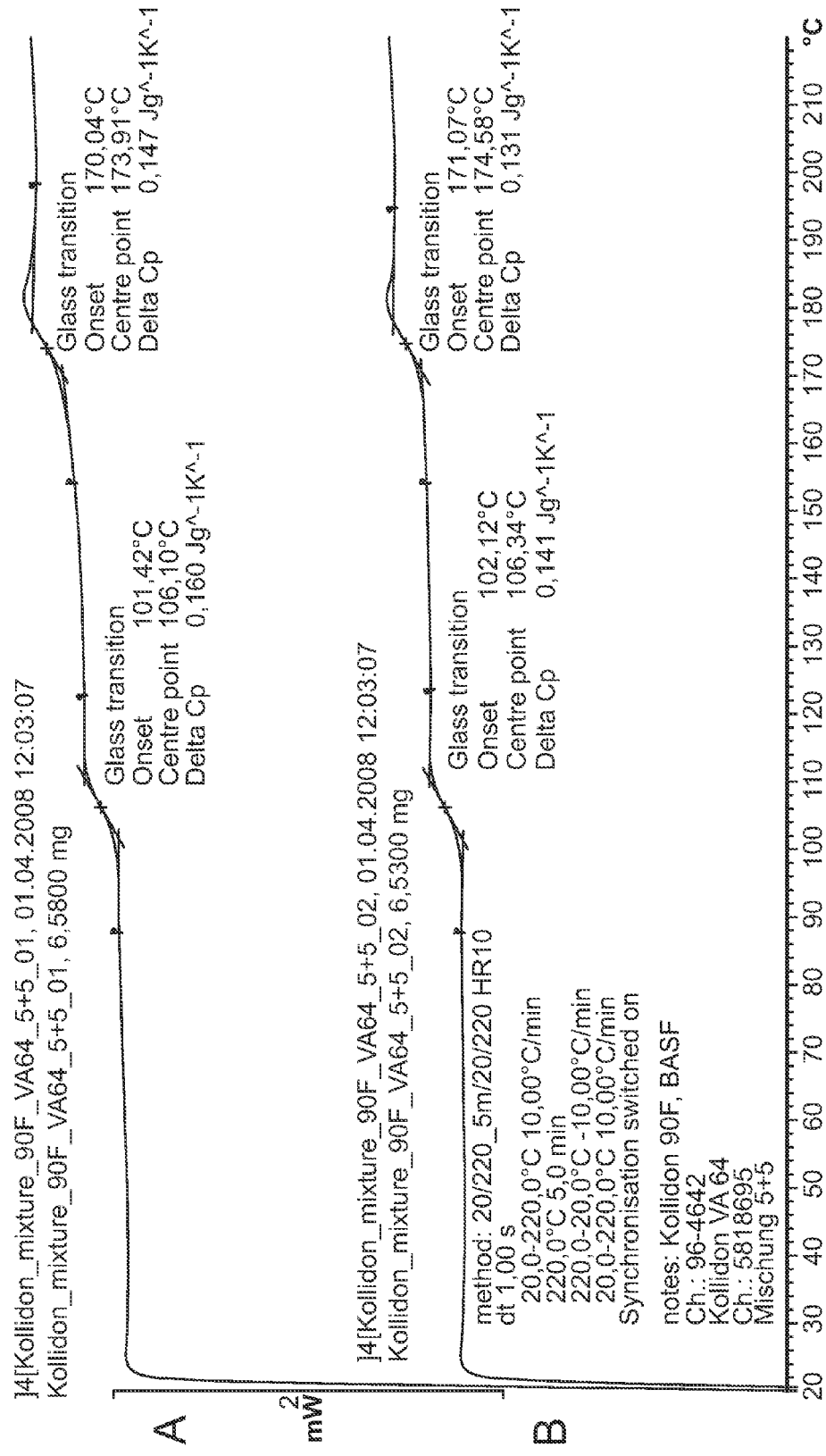

| | | |
|---|---|---|
| 2008/0248117 A1 | 10/2008 | Kolter et al. |
| 2009/0012184 A1 | 1/2009 | Rosenberg et al. |
| 2009/0247591 A1 | 10/2009 | Zemolka et al. |

FOREIGN PATENT DOCUMENTS

| | | |
|---|---|---|
| EP | 1690528 A1 | 8/2006 |
| JP | 2008519067 A | 6/2008 |
| JP | 2011515431 A | 5/2011 |
| WO | 9726866 A1 | 7/1997 |
| WO | 2006049433 A1 | 5/2006 |
| WO | 2006131481 A1 | 12/2006 |
| WO | 2007/003278 A1 | 1/2007 |
| WO | 2007/138997 A1 | 6/2007 |

OTHER PUBLICATIONS

Form PCT/ISA/210, WO, Oct. 28, 2009, Abbott GmbH & Co. KG.
Form PCT/ISA/237, WO, Oct. 28, 2009, Abbott GMbH & Co. KG.
"Kollidon K8," Chemical Information Search, http://www.chemindustry.com/chemicals/0210024.html, accessed Jul. 7, 2013, p. 1.
Buhler, "Kollidon, Polyvinylpyrrolidone Excipients for the Pharmaceutical Industry," BASF, Chapters 2 and 4, Mar. 2008.
T. Rades, "Formulation and Stability of Amorphous Forms-A Practical Guide" The New Zealand National School of Pharmacy, University of Otago, Dunedin, NZ (Oct. 26, 2006).
English translation of an Office Action Issued in Japanese Application 2014-246982, dated Dec. 1, 2015.

PHARMACEUTICAL DOSAGE FORM COMPRISING POLYMERIC CARRIER COMPOSITION

This application a continuation of U.S. application Ser. No. 13/001,060, which is the U.S. national phase, pursuant to 35 U.S.C. §371, of PCT international application Ser. No. PCT/EP2009/058187, filed Jun. 30, 2009, designating the United States and published in English on Jan. 7, 2010 as publication WO 2010/000740 A1, which claims priority to European patent application No. 08159367.5, filed Jun. 30, 2008. The entire contents of the aforementioned patent applications are incorporated herein by this reference.

The present invention relates to a pharmaceutical dosage form, in particular a dosage form for oral administration, which comprises a solid dispersion product of an active ingredient dispersed in a polymeric carrier composition and a method of preparing the dosage form.

A measure of the potential usefulness of an oral dosage form of an active pharmaceutical ingredient (also referred to as "drug") is the bioavailability observed after oral administration of the dosage form. Various factors can affect the bioavailability of a drug administered orally. These factors include aqueous solubility, drug absorption throughout the gastrointestinal tract, dosage strength and first-pass effect. Aqueous solubility is one of the most important of these factors. Unfortunately, the crystalline forms of many known drugs are characterized by a poor solubility in aqueous liquids, which affects their dissolution rate and bioavailability.

There have been attempts to improve the bioavailability provided by solid dosage forms by forming solid dispersions of the drug. Solid dispersions are preferred physical systems because the components therein readily form liquid solutions when contacted with a liquid medium such as gastric juice. The ease of dissolution may be attributed at least in part to the fact that the energy required for dissolution of the components from a solid dispersion is less than that required for the dissolution of the components from a bulk crystalline solid phase.

Formation of solid dispersions as a means to enhance the dissolution rate of poorly soluble active ingredients typically involves hydrophilic polymer systems. An obstacle of solid dispersion technology in pharmaceutical product development is that a large amount of carrier has been required to transform a crystalline drug stably in a dispersed or amorphous state.

Melt-processing techniques are frequently used to form solid dispersions. These methods involve preparing a homogeneous melt of the active ingredient and the hydrophilic polymer, e.g. by feeding a powder blend through a hot-melt extruder. In order to obtain adequate homogenization and dissolution of the drug, the viscosity of the melt must be sufficiently low. As the melt viscosity of polymers generally decreases at higher temperatures, employing a high enough temperature would result in superior homogenization and dissolution of the drug. However, bulk melting and mixing steps at elevated temperatures may expose the drug to a "heat history", wherein the purity and potency of the drug is diminished to a significant extent.

Incorporation of certain additives into the melt, which cause plasticization of the polymer, helps to dissolve the drug at somewhat lower temperatures. High amounts of such additives, however, tend to deteriorate the mechanical properties and the storage stability of the dosage forms and to make the drug more susceptible to recrystallization.

WO 97/26866 discloses the preparation of non-steroidal analgesics which are obtained through extrusion and moulding of a melt containing a mixture of a homopolymer of N-vinylpyrrolidone with a Fikentscher K value of 30, a water-soluble copolymer of N-vinylpyrrolidone and a physiologically acceptable sodium or potassium salt.

In a paper entitled "Formulation and stability of amorphous forms—a practical guide", T. Rades describes an example of a miscible excipient mixture consisting of a mixture of Kollidone 17 and Kollidone 30.

There is a continuing need for the development of improved solid dosage forms. Particularly sought after are polymeric carrier compositions for the formation of solid dispersions that exhibit higher drug dissolution power and/or allow a reduction of the viscosity of the melt without deteriorating the mechanical properties and storage stability of the dosage form.

It has now been found that certain hydrophilic polymers can be mixed homogeneously and have only one glass transition temperature. These polymer alloys are of great interest due to their extraordinary thermal and mechanical properties.

The invention relates to a pharmaceutical dosage form which comprises a solid dispersion product of at least one active ingredient dispersed in a polymeric carrier composition, the polymeric carrier composition comprising a) a vinylpyrrolidone homopolymer having a molecular weight distribution such that at least 95% by weight of the homopolymer has a molecular weight within the range of from 1000 to 13 000; and b) a vinylpyrrolidone copolymer having a weight-average molecular weight of from 5000 to 1 500 000.

The vinylpyrrolidone copolymer has a weight-average molecular weight of from 5000 to 1 500 000, preferably 10 000 to 80 000. It may be selected from water-soluble, pharmaceutically acceptable vinylpyrrolidone copolymers. When dissolved at 20° C. in an aqueous solution at 2% (w/v), the copolymer preferably has an apparent viscosity of 1 to 5000 mPa·s, more preferably of 1 to 700 mPa·s, and most preferably of 5 to 100 mPa·s.

In preferred embodiments, the ratio of the weight-average molecular weight of the vinylpyrrolidone copolymer to its number-average molecular weight (Mw/Mn) is in the range of from 1.5 to 5.0, preferably 2.0 to 4.5. It is believed that a ratio Mw/Mn within this range is favourable with respect to the hardness and abrasion resistance of the solid dispersion product.

Preferably, the vinylpyrrolidone copolymer employed in the invention has a Tg of at least 40° C., preferably at least +50° C., most preferably from 80° to 180. ° C. "Tg" means glass transition temperature. Methods for determining the Tg values of organic polymers are described in "Introduction to Physical Polymer Science", 2nd Edition, by L. H. Sperling, published by John Wiley & Sons, Inc., 1992. The Tg value can be calculated as the weighted sum of the Tg values for homopolymers derived from each of the individual monomers, i, that make up the polymer: $Tg=\Sigma W_i X_i$ where W is the weight percent of monomer i in the organic polymer, and X is the Tg value for the homopolymer derived from monomer i. Tg values for the homopolymers can be found in the "Polymer Handbook", 2nd Edition, J. Brandrup and E. H. Immergut, Editors, published by John Wiley & Sons, Inc., 1975.

The vinylpyrrolidone copolymer used in this invention contains N-vinyl-2-pyrrolidone (hereinafter also simply referred to as vinylpyrrolidone) monomer and at least one comonomer other than vinylpyrrolidone. In general, the vinylpyrrolidone copolymer comprises from 20 to 80%, preferably 30 to 70%, by weight of vinylpyrrolidone units, relative to the total weight of the copolymer.

The comonomer may be suitably selected from carboxylate group-containing monomers, such as crotonic acid or maleic anhydride; or amine or amide group-containing comonomers such as vinylamine, N,N'-dimethylacrylamide, dialkylamino alkylacrylate or methacrylate, e.g. dimethylaminoethylacrylate or methacrylate, dialkylaminoalkyl styrene, e.g. dimethylaminomethyl styrene, or N-vinyl imidazole. The amine group-containing comonomers can be unquaternized or quaternized as in the case of GAFQUAT-734 (the 50% quaternized copolymer of 80% N-vinyl-2-pyrrolidone and 20% dimethylaminoethyl methacrylate).

The preferred comonomers, however, are vinylesters such as vinylacetate or vinylpropionate. Vinylacetate is the most preferred comonomer.

A particularly preferred vinylpyrrolidone copolymer is a copolymer of 60% by weight of the copolymer, N-vinyl pyrrolidone, and 40% by weight of the copolymer, vinyl acetate, which is available from BASF SE, Ludwigshafen, Germany, as Kollidone VA64 or Kollidone K28.

Vinylpyrrolidone homopolymers are also referred to as polyvinylpyrrolidone (PVP). The vinylpyrrolidone homopolymer useful in the invention has a molecular weight distribution such that at least 95% by weight of the polymer have a molecular weight within the range of from 1000 to 13 000 preferably within the range of from 2000 to 11 000.

Different grades of vinylpyrrolidone homopolymers which are useful in the invention are commercially available, such as PVP K12, PVP K15, or PVP K17. The K-value referred to in this nomenclature is calculated by Fikentscher's formula from the viscosity of the PVP in aqueous solution, relative to that of water. A particularly preferred vinylpyrrolidone homopolymer to be employed in this invention consists of PVP K12 or PVP K17 or a mixture of both.

In preferred embodiments, the polymeric carrier composition exhibits a single glass transition temperature Tg as measured by differential scanning calorimetry (DSC). In general, the Tg takes an intermediate position between the corresponding glass transition temperatures of the vinylpyrrolidone copolymer and the vinylpyrrolidone homopolymer. The occurrence of a single Tg indicates that the individual polymers are blended into one another on a molecular level to obtain a polymer alloy or homogeneous system which consists of one phase as defined in thermodynamics.

In general, the weight ratio of a) the vinylpyrrolidone homopolymer to b) the vinylpyrrolidone copolymer is in the range of from 5:95 to 50:50, preferably of from 10:90 to 40:60.

In the dosage forms of the invention, the active ingredient is present as a solid dispersion or, preferably, as a solid solution. The term "solid dispersion" defines a system in a solid state (as opposed to a liquid or gaseous state) comprising at least two components, wherein one component is dispersed evenly throughout the other component or components. The term "solid dispersion" encompasses systems having small particles, typically of less than 1 μm in diameter, of one phase dispersed in another phase.

In preferred solid solutions, the active ingredient is molecularly dispersed in the polymeric carrier composition. Typically, these systems are chemically and physically uniform or homogeneous throughout or consist of one phase (as defined in thermodynamics). Such a solid dispersion is also called a "solid solution" or a "glassy solution". A glassy solution is a homogeneous, glassy system in which a solute is dissolved in a glassy solvent. Glassy solutions and solid solutions are preferred physical systems. These systems do not contain any significant amounts of active ingredients in their crystalline or microcrystalline state, as evidenced by thermal analysis (DSC) or X-ray diffraction analysis (WAXS).

The dosage forms according to the invention are characterized by an excellent stability and, in particular, exhibit high resistance against recrystallization or decomposition of the active ingredient(s).

The solid dispersion product may additionally comprise at least one additive selected from solubilizers, flow regulators, disintegrants, bulking agents and lubricants.

In an embodiment, the dosage form according to the invention is obtained by a method which comprises:
a) preparing a liquid mixture containing the at least one active agent, the polymeric carrier composition and at least one solvent, and
b) removing the solvent(s) from the liquid mixture to obtain a solid dispersion product.

In an other embodiment, the dosage form according to the invention is obtained by a method which comprises:
a) preparing a homogeneous melt of said at least one active ingredient and the polymeric carrier composition, and
b) allowing the melt to solidify to obtain a solid dispersion product.

Optionally, the solid dispersion product is grinded and compressed into a tablet.

Generally, the solid dispersion product comprises, relative to the total weight of the solid dispersion product, from about 0.001 to 80% by weight, preferably from about 5 to 50% by weight, of at least one active ingredient.

Generally, the solid dispersion product comprises, relative to the total weight of the solid dispersion product, from about 99.99 to 20% by weight, preferably from about 95 to 50% by weight, of the polymeric carrier composition.

In preferred embodiments, the solid dispersion product comprises, relative to the total weight of the solid dispersion product, from about 0.1 to 40% by weight, preferably from about 0.5 to 10% by weight, of at least one pharmaceutically acceptable solubilizer.

Whereas the dosage form of the invention may consist entirely of solid dispersion product, additives and adjuvants are usually used in formulating the solid dispersion product into the dosage forms. Generally, the dosage form comprises at least 10% by weight, preferably at least 40% by weight, and most preferably at least 45% by weight, of solid dispersion product, based on the total weight of the solid dosage form.

Pharmaceutically active ingredients are biologically active agents and include those which exert a local physiological effect, as well as those which exert a systemic effect, after oral administration. The invention is particularly useful for water-insoluble or poorly water-soluble (or "hydrophobic" or "lipophilic") compounds. Compounds are considered water-insoluble or poorly water-soluble when their solubility in water at 25° C. is less than 1 g/100 ml, especially less than 0.1 g/100 ml.

Examples of suitable pharmaceutically active ingredients include, but are not limited to:

analgesic and anti-inflammatory drugs such as fentanyl, indomethacin, ibuprofen, naproxene, diclofenac, diclofenac sodium, fenoprofen, acetylsalicylic acid, ketoprofen, nabumetone, paracetamol, piroxicam, meloxicam, tramadol, and COX-2 inhibitors such as celecoxib and rofecoxib;

anti-arrhythmic drugs such as procainamide, quinidine and verapamil;

antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxime and streptomycin;

anti-coagulants such as warfarin;

antidepressants such as amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;

anti-diabetic drugs such as glibenclamide and metformin;

anti-epileptic drugs such as carbamazepine, clonazepam, ethosuximide, gabapentin, lamotrigine, levetiracetam, phenobarbitone, phenyloin, primidone, tiagabine, topiramate, valpromide and vigabatrin;

antifungal agents such as amphotericin, clotrimazole, econazole, fluconazole, flucytosine, griseofulvin, itraconazole, ketoconazole, miconazole nitrate, nystatin, terbinafine and voriconazole;

antihistamines such as astemizole, cinnarizine, cyproheptadine, decarboethoxyloratadine, fexofenadine, flunarizine, levocabastine, loratadine, norastemizole, oxatomide, promethazine and terfenadine;

anti-hypertensive drugs such as captopril, enalapril, ketanserin, lisinopril, minoxidil, prazosin, ramipril, reserpine, terazosin and telmisartan;

anti-muscarinic agents such as atropine sulphate and hyoscine;

antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinorelbine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chiormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibodies such as trastuzumab; podophyllotoxin derivatives such as etoposide and teniposide; farnesyl transferase inhibitors; anthrachinon derivatives such as mitoxantron; tyrosine kinase inhibitors such as gleevec; PARP inhibitors; BCL2 inhibitors;

anti-migraine drugs such as alniditan, naratriptan and sumatriptan;

anti-Parkinsonian drugs such as bromocryptine mesylate, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;

anti-stroke agents such as lubeluzole, lubeluzole oxide, riluzole, aptiganel, eliprodil and remacemide;

antitussives such as dextromethorphan and laevodropropizine;

antivirals such as acyclovir, ganciclovir, loviride, tivirapine, zidovudine, lamivudine, zidovudine/lamivudine, didanosine, zalcitabine, stavudine, abacavir, lopinavir, amprenavir, nevirapine, efavirenz, delavirdine, indinavir, nelfinavir, ritonavir, saquinavir, adefovir and hydroxyurea;

beta-adrenoceptor blocking agents such as atenolol, carvedilol, metoprolol, nebivolol and propanolol;

cardiac inotropic agents such as aminone, digitoxin, digoxin and milrinone;

corticosteroids such as beclomethasone dipropionate, betamethasone, budesonide, dexamethasone, hydrocortisone, methylprednisolone, prednisolone, prednisone and triamcinolone;

disinfectants such as chlorhexidine;

diuretics such as acetazolamide, furosemide, hydrochlorothiazide and isosorbide;

enzymes;

gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;

haemostatics such as aminocaproic acid;

HIV protease inhibiting compounds such as ritonavir, lopinavir, indinavir, saquinavir, 5(S)-Boc-amino-4(S)-hydroxy-6-phenyl-2(R)phenylmethylhexanoyl-(L)-Val-(L)-Phe-morpholin-4-ylamide, 1-Naphthoxyacetyl-beta-methylthio-Ala-$(2S,3S)_3$-amino-2-hydroxy-4-butanoyl 1,3-thiazolidine-4-t-butylamide, 5-isoquinolinoxyacetyl-beta-methylthio-Ala-(2S,3S)-3-amino-2-hydroxy-4-butanoyl-1,3-thiazolidine-4-t-butylamide, [1S—[1R—(R—),2S*])—N'-[3-[[[(1,1-dimethylethyl)amino]carbonyl](2-methylpropyl)amino]-2hydroxy-1-(phenylmethyl)propyl]-2-[(2-quinolinylcarbonyl)amino]-butanediamide, amprenavir; DMP-323; DMP-450; nelfinavir, atazanavir, tipranavir, palinavir, darunavir, RO033-4649, fosamprenavir, P-1946, BMS 186,318, SC-55389a; BILA 1906 BS, tipranavir;

lipid regulating agents such as atorvastatin, fenofibrate, fenofibric acid, lovastatin, pravastatin, probucol and simvastatin;

local anaesthetics such as benzocaine and lignocaine;

opioid analgesics such as buprenorphine, codeine, dextromoramide, dihydrocodeine, hydrocodone, oxycodone and morphine;

parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;

peptides and proteins such as antibodies, becaplermin, cyclosporine, tacrolimus, erythropoietin, immunoglobulins and insuline;

sex hormones such as oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone and quingestanol acetate;

stimulating agents such as sildenafil, vardenafil;

vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate;

their N-oxides, their pharmaceutically acceptable acid or base addition salts and their stereochemically isomeric forms.

Pharmaceutically acceptable acid addition salts comprise the acid addition salt forms which can be conveniently obtained by treating the base form of the active ingredient with appropriate organic and inorganic acids.

Active ingredients containing an acidic proton may be converted into their non-toxic metal or amine addition salt forms by treatment with appropriate organic and inorganic bases.

The term "addition salt" also comprises the hydrates and solvent addition forms which the active ingredients are able to form. Examples of such forms are hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

The solid dispersion product may contain one or more plasticizers. The amount of plasticizer preferably does not exceed 15% by weight, and more preferably does not exceed 5% by weight, relative to the total weight of the solid dispersion product. Plasticizers useful in the present invention comprise organic, preferably non-volatile compounds, such as, for example, $C_7$-$C_{30}$-alkanols, ethylene glycol, propylene glycol, glycerol, trimethylolpropane, triethylene glycol, butandiols, pentanols such as pentaerythritol and hexanols, polyalkylene glycols, preferably having a molecular weight of from 200 to 1 000, such as, for example, polyethylene glycols (e.g. PEG 300, PEG 400), polypropylene glycols and polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters, in particular triethylcitrate), fatty acid esters such as glycerol mono-, di- or triacetate or sodium diethyl sulfosuccinate. Particularly preferred plasticizers are selected from the group consisting of glyceryl triacetate, triethyl citrate, polyethylene glycol and mixtures thereof.

The solid dispersion product may comprise at least one pharmaceutically acceptable solubilizer. The term "pharmaceutically acceptable solubilizer" as used herein refers to a pharmaceutically acceptable non-ionic surfactant. The solubilizer may effectuate an instantaneous emulsification of the active ingredient released from the dosage form and/or prevent precipitation of the active ingredient in the aqueous fluids of the gastrointestinal tract. A single solubilizer as well as combinations of solubilizers may be used.

Preferred solubilizers are selected from sorbitan fatty acid esters, polyalkoxylated fatty acid esters such as, for example, polyalkoxylated glycerides, polyalkoxylated sorbitan fatty acid esters or fatty acid esters of polyalkylene glycols, polyalkoxylated ethers of fatty alcohols, tocopheryl compounds or mixtures of two or more thereof. A fatty acid chain in these compounds ordinarily comprises from 8 to 22 carbon atoms. The polyalkylene oxide blocks comprise on average from 4 to 50 alkylene oxide units, preferably ethylene oxide units, per molecule.

Suitable sorbitan fatty acid esters are sorbitan monolaurate, sorbitan monopalmitate, sorbitan monostearate (Span® 60), sorbitan monooleate (Span® 80), sorbitan tristearate, sorbitan trioleate, sorbitan monostearate, sorbitan monolaurate or sorbitan monooleate.

Examples of suitable polyalkoxylated sorbitan fatty acid esters are polyoxyethylene (20) sorbitan monolaurate, polyoxyethylene (20) sorbitan monopalmitate, polyoxyethylene (20) sorbitan monostearate, polyoxyethylene (20) sorbitan monooleate (Tween® 80), polyoxyethylene (20) sorbitan tristearate (Tween® 65), polyoxyethylene (20) sorbitan trioleate (Tween® 85), polyoxyethylene (4) sorbitan monostearate, polyoxyethylene (4) sorbitan monolaurate or polyoxyethylene (4) sorbitan monooleate.

Suitable polyalkoxylated glycerides are obtained for example by alkoxylation of natural or hydrogenated glycerides or by transesterification of natural or hydrogenated glycerides with polyalkylene glycols. Commercially available examples are polyoxyethylene glycerol ricinoleate 35, polyoxyethylene glycerol trihydroxystearate 40 (Cremophor® RH40, BASF AG) and polyalkoxylated glycerides like those obtainable under the proprietary names Gelucire® and Labrafil® from Gattefosse, e.g. Gelucire® 44/14 (lauroyl macrogol 32 glycerides prepared by transesterification of hydrogenated palm kernel oil with PEG 1500), Gelucire® 50/13 (stearoyl macrogol 32 glycerides, prepared by transesterification of hydrogenated palm oil with PEG 1500) or Labrafil M1944 CS (oleoyl macrogol 6 glycerides prepared by transesterification of apricot kernel oil with PEG 300).

A suitable fatty acid ester of polyalkylene glycols is, for example, PEG 660 hydroxystearic acid (polyglycol ester of 12-hydroxystearic acid (70 mol %) with 30 mol % ethylene glycol).

Suitable polyalkoxylated ethers of fatty alcohols are, for example, PEG (2) stearyl ether (Brij® 72), macrogol 6 cetylstearyl ether or macrogol 25 cetylstearyl ether.

In general, the tocopheryl compound corresponds to the formula below

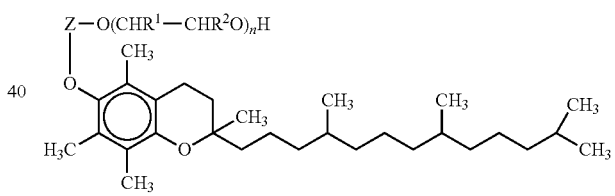

wherein Z is a linking group, R1 and R2 are, independently of one another, hydrogen or $C_{104}$ alkyl and n is an integer from 5 to 100, preferably 10 to 50. Typically, Z is the residue of an aliphatic dibasic acid such as glutaric, succinic, or adipic acid. Preferably, both R1 and R2 are hydrogen.

The preferred tocopheryl compound is alpha tocopheryl polyethylene glycol succinate, which is commonly abbreviated as vitamin E TPGS. Vitamin E TPGS is a water-soluble form of natural-source vitamin E prepared by esterifying d-alpha-tocopheryl acid succinate with polyethylene glycol 1000. Vitamin E TPGS is available from Eastman Chemical Company, Kingsport, Tenn., USA and is listed in the US pharmacopoeia (NF).

In addition to the vinylpyrrolidone homopolymer and vinylpyrrolidone copolymer defined above, the polymeric carrier composition may comprise other pharmaceutically acceptable polymers. These may be selected from
cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate;

high molecular polyalkylene oxides such as polyethylene oxide and polypropylene oxide and copolymers of ethylene oxide and propylene oxide, polyvinyl alcohol-polyethylene glycol-graft copolymers (available as Kollicoat® IR from BASF AG, Ludwigshafen, Germany);

polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, oligo- and polysaccharides such as carrageenans, galactomannans and xanthan gum, or mixtures of one or more thereof.

A further polymer which can be suitably used is Kollidon® SR (available from BASF AG, Ludwigshafen, Germany) which comprises a mixture of PVP and polyvinylacetate.

The solid dispersion product may be prepared by a variety of methods. One such method is the solvent evaporation method. In a solvent evaporation method, the at least one active ingredient, the polymeric carrier composition and the optional ingredients of the solid dispersion product are dissolved in a common solvent or combination of solvents and the solvents are subsequently removed from the solution by evaporation.

Suitable solvents are those which are capable of dissolving or solubilising the active ingredient as well as the vinylpyrrolidone homopolymer and the vinylpyrrolidone copolymer which constitute the polymeric carrier composition. Any such solvent may be used, however, pharmaceutically acceptable solvents are preferred because traces of solvent may remain in the dried solid dispersion product. Suitably, the solvent may be selected from the group consisting of alkanols, such as methanol, ethanol, isopropanol, n-propanol, isobutanol, n-butanol; hydrocarbons, such as pentane, hexane, cyclohexane, methylcyclohexane, toluene, xylene; halogenated hydrocarbons, such as dichloromethane, trichloromethane, dichloroetane, chlorobenzene; ketons, such as acetone; esters, such as ethyl acetate; ethers, such as dioxane, tetrahydrofurane; and combinations of two or more thereof. Ethanol is particularly preferred due to its availability, dissolving power and pharmaceutical safeness.

The liquid mixture may be prepared by any suitable method of contacting the ingredients thereof, i.e. the vinylpyrrolidone homopolymer and the vinylpyrrolidone copolymer, active agent, the optional ingredients and the solvent or combination of solvents. In an embodiment, the liquid mixture is prepared by dissolving the vinylpyrrolidone homopolymer and the vinylpyrrolidone copolymer to obtain a polymeric carrier solution, and adding the active agent to the solution. The dissolved polymeric carrier composition may exert a solubilityenhancing effect on the active agent; thus, the solubility of the active agent in the polymeric carrier solution may be several times higher than its solubility in the solvent alone.

The liquid mixture has a dry matter content of up to 90% by weight, for example 0.5 to 90% by weight, in most instances 2 to 60% by weight, relative to the total weight of the liquid mixture.

The solvent(s) may be removed by any suitable method known in the art, such as spray-drying, drum drying, belt drying, tray drying or combinations of two or more thereof.

In spray-drying, the liquid to be dried is suspended in a gas flow, e.g., air, i.e. the liquid is converted into a fog-like mist (atomized), providing a large surface area. The atomized liquid is exposed to a flow of hot gas in a drying chamber. The moisture evaporates quickly and the solids are recovered as a powder consisting of fine, hollow spherical particles. Gas inlet temperatures of up to 250° C. or even higher may be used, due to the evaporation the gas temperature drops very rapidly to a temperature of about 30 to 150° C. (outlet temperature of the gas).

The principle of the drum drying process (roller drying) is that a thin film of material is applied to the smooth surface of a continuously rotating, heated metal drum. The film of dried material is continuously scraped off by a stationary knife located opposite the point of application of the liquid material.

In a belt dryer, the liquid is spread or sprayed onto a belt which passes over several heated plates underneath the belt. The material is heated by steam-heated or electrically heated plates. The evaporation of the solvent can additionally be fostered by infrared radiators or microwave radiators located over the belt.

In tray drying, the liquid mixture is distributed over a number of trays. These are placed in an oven, usually in a stream of hot gas, e.g. air. Vacuum may be applied additionally.

The dried solid dispersion product may then be grinded and/or classified (sieved).

The dried solid dispersion product may then be filled into capsules or may be compacted. Compacting means a process whereby a powder mass comprising the solid dispersion product is densified under high pressure in order to obtain a compact with low porosity, e.g. a tablet. Compression of the powder mass is usually done in a tablet press, more specifically in a steel die between two moving punches.

In a separate aspect of the invention, a solid dispersion product may also be obtained by spray coating, i.e. by spraying the liquid mixture onto preformed cores. The term "spray coating" is used conventionally and refers to the coating or layering of the active ingredient/polymeric carrier composition onto a core. The term core is used broadly to describe any solid substrate onto which the liquid mixture may be sprayed, so that the solid dispersion forms as a layer on the core.

Preferably, the core has a solubility in the spray-coating solution of less than 10 wt %; more, preferably less than 5 wt %; still more preferably less than 1 wt %. The core may be pharmaceutical inert. The core may be a solid particle or object, which does not disintegrate in the relevant body fluid. Alternatively, the core may comprise a disintegrating agent which will cause the layered particle to disrupt in the relevant body fluid. The core is mainly intended for carrying the layer(s) of the solid dispersion product. Examples of core materials are sugar beads, wax beads, glass beads, lactose, microcrystalline cellulose, polymer beads, starch, colloidal silica, calcium phosphate, calcium carbonate, and calcium containing salts and excipients, etc. The core may be made by any known method, such as melt- or spray-congealing, extrusion/spheronization, granulation, spray-drying and the like.

Alternatively, the core may be a dosage form such as a tablet, pill, multiparticulate or capsule. The dosage form may contain the same or a different drug, and may provide either immediate or controlled release. Spray-coating a amorphous drug onto the dosage form may be useful for a combination therapy of different drugs.

The cores may have any shape, size, and size distribution. In one embodiment, the core is generally spherical with a smooth surface. In another embodiment, the cores range in size of from about 1 μm to about 3000 μm, preferably from about 10 μm to about 1000 μm, more preferably from about 50 μm to about 500 μm. To obtain a uniform final product it is generally desired to use cores with a narrow size distribution.

The core may be an agglomerate, a granule, or a particle which has been layered with one or more layer(s) in accordance with the invention. Core agglomerates and granules can be made by any method conventionally used in the art, such as spray-drying, vacuum drying, or spray granulation.

Preferably, the solid dispersion product is prepared by melt-extrusion. The melt-extrusion process comprises the steps of preparing a homogeneous melt of the active ingredient or combination of active ingredients, the polymeric carrier composition and the optional ingredients of the solid dispersion product, and cooling the melt until it solidifies. "Melting" means a transition into a liquid or rubbery state in which it is possible for one component to become homogeneously embedded in the other. Typically, one component will melt and the other components will dissolve in the melt, thus forming a solution. Melting usually involves heating above the softening point of the pharmaceutically acceptable polymer. The preparation of the melt can take place in a variety of ways. The mixing of the components can take place before, during or after the formation of the melt. For example, the components can be mixed first and then melted or simultaneously mixed and melted. Usually, the melt is homogenized in order to disperse the active ingredients efficiently. Also, it may be convenient to melt the pharmaceutically acceptable polymer first and then to admix and homogenize the active ingredients.

The melt temperature is usually in the range of 70 to 250° C., preferably in the range of 80 to 180° C. and most preferably in the range of 100 to 140° C.

In order to prevent the admission of air to the process and thereby to avoid oxidation and other disadvantageous influence on the active ingredient or other constituents of the melt, the process may be carried out in an atmosphere of protective gas, preferably an inert gas such as nitrogen or carbon dioxide.

The active ingredients can be employed as such or as a solution or dispersion in a suitable solvent such as alcohols, aliphatic hydrocarbons or esters. Another solvent which can be used is liquid carbon dioxide. The solvent is removed, e.g. evaporated, upon preparation of the melt.

Various additives may be included in the melt, for example flow regulators such as colloidal silica; lubricants, bulking agents (fillers), disintegrants, plasticizers, stabilizers such as antioxidants, light stabilizers, radical scavengers, or stabilizers against microbial attack.

The melting and/or mixing takes place in an apparatus customary for this purpose. Particularly suitable are extruders or kneaders. Suitable extruders include single screw extruders, intermeshing screw extruders or other multiscrew extruders, preferably twin screw extruders, which can be co-rotating or counter-rotating and optionally equipped with kneading disks or other screw elements for mixing or dispersing the melt. It will be appreciated that the working temperatures will also be determined by the kind of extruder or the kind of configuration within the extruder used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The extrudate exiting from the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. A broad range of tablet forms can be attained by using rollers with different forms of depressions. If the rollers do not have depressions on their surface, films can be obtained. Alternatively, the extrudate is moulded into the desired shape by injection-moulding. Alternatively, the extrudate is subjected to profile extrusion and cut into pieces, either before (hot-cut) or after solidification (cold-cut).

Additionally, foams can be formed if the extrudate contains a propellant such as a gas, e.g. carbon dioxide, or a volatile compound, e.g. a low molecular-weight hydrocarbon, or a compound that is thermally decomposable to a gas. The propellant is dissolved in the extrudate under the relatively high pressure conditions within the extruder and, when the extrudate emerges from the extruder die, the pressure is suddenly released. Thus the solvability of the propellant is decreased and/or the propellant vaporises so that a foam is formed.

Optionally, the resulting solid solution product is milled or ground to granules. The granules may then be filled into capsules or may be compacted. Compacting means a process whereby a powder mass comprising the granules is densified under high pressure in order to obtain a compact with low porosity, e.g. a tablet. Compression of the powder mass is usually done in a tablet press, more specifically in a steel die between two moving punches.

At least one additive selected from flow regulators, disintegrants, bulking agents (fillers) and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Suitable bulking agents (also referred to as "fillers") are selected from lactose, calcium hydrogenphosphate, microcrystalline cellulose (Avicel®), magnesium oxide, potato or corn starch, isomalt, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, talc, and the like.

Various other additives may be used, for example dyes such as azo dyes, organic or inorganic pigments such as aluminium oxide or titanium dioxide, or dyes of natural origin; stabilizers such as antioxidants, light stabilizers, radical scavengers, or stabilizers against microbial attack.

Dosage forms according to the invention may be provided as dosage forms consisting of several layers, for example laminated or multilayer tablets. They can be in open or closed form. "Closed dosage forms" are those in which one layer is completely surrounded by at least one other layer. Multilayer forms have the advantage that two active ingredients which are incompatible with one another can be processed, or that the release characteristics of the active ingredient(s) can be controlled. For example, it is possible to provide an initial dose by including an active ingredient in one of the outer layers, and a maintenance dose by including the active ingredient in the inner layer(s). Multilayer tablets types may be produced by compressing two or more layers of granules. Alternatively, multilayer dosage forms may be produced by a process known as "coextrusion". In essence, the process comprises the preparation of at least two different melt compositions as explained above, and passing these molten compositions into a joint coextrusion die. The shape of the coextrusion die depends on the required drug form. For example, dies with a plain die gap, called slot dies, and dies with an annular slit are suitable.

In order to facilitate the intake of such a dosage form by a mammal, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. If desired, the film coat may be an enteric coat. The film coat usually includes a polymeric film-forming material such as hydroxypropyl methylcellulose, hydroxypropyl cellulose, and acrylate or methacrylate copolymers. Besides a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as anti-adhesive. The film coat usually accounts for less than about 5% by weight of the dosage form.

The following example and the accompanying figures will serve to further illustrate the invention without limiting it.

Figure 2:
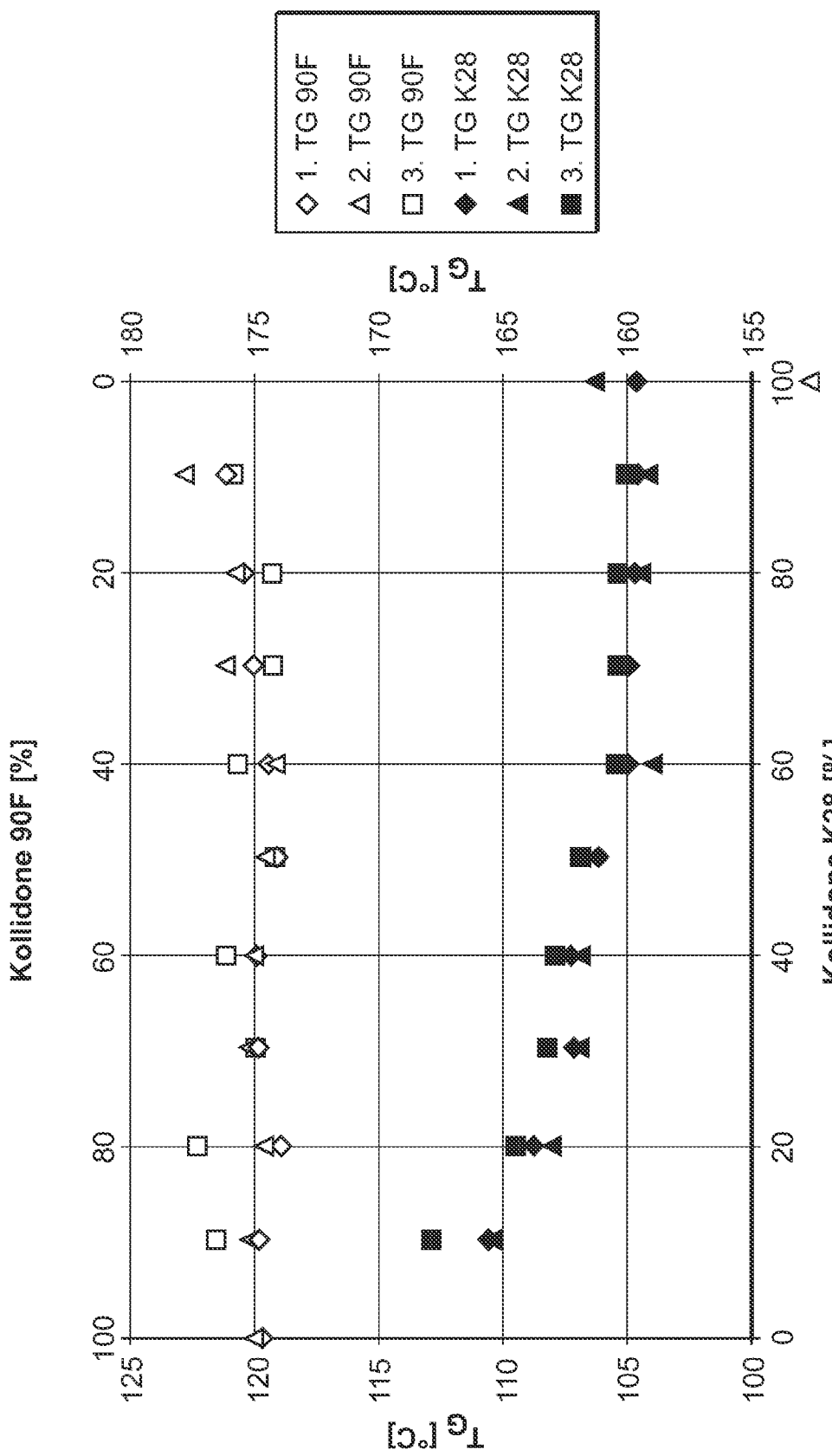
Figure 5:
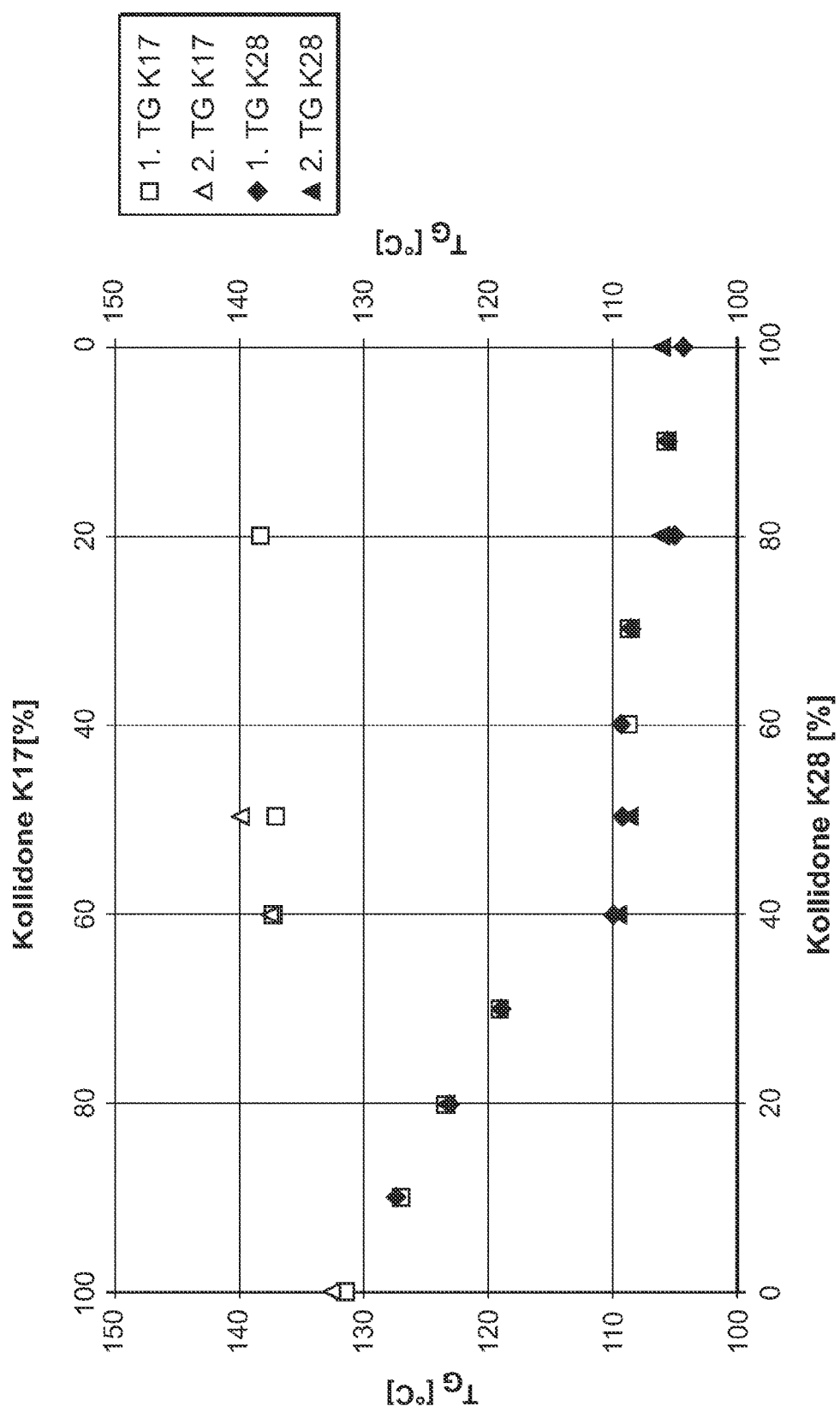

FIGS. 1A and B show DSC thermograms of a 50/50 (by weight) mixture of Kollidone VA64/Kollidone 90F (experiment performed in duplicate; i.e., two measurements, shown in FIGS. 1A and B, using samples having the same composition, which, for better comparability, are depicted together using the same x-axis);

FIG. 2 shows a plot of glass transition temperatures of Kollidone VA64/Kollidone 90F mixtures versus composition of the mixture;

FIGS. 3A and B show DSC thermograms of a 60/40 (by weight) mixture of Kollidone VA64/Kollidone K17 (experiment performed in duplicate; i.e., two measurements, shown in FIGS. 3A and B, using samples having the same composition, which, for better comparability, are depicted together using the same x-axis);

FIGS. 4A and B show DSC thermograms of a 40/60 (by weight) mixture of Kollidone VA64/Kollidone K17 (experiment performed in duplicate; i.e., two measurements, shown in FIGS. 4A and B, using samples having the same composition, which, for better comparability, are depicted together using the same x-axis);

FIG. 5 shows a plot of glass transition temperatures of Kollidone VA64/Kollidone K17 mixtures versus composition of the mixture.

EXAMPLE

Kollidone VA64 (copolymer of 60% by weight of the copolymer, N-vinyl pyrrolidone and 40% by weight of the copolymer, vinyl acetate), Kollidone K17 (polyvinylpyrrolidone Mw between 7000 and 11 000 and Kollidone 90F (polyvinylpyrrolidone Mw between 1 000 000 and 1 500 000) were purchased from BASF SE, Ludwigshafen, Germany.

Powdery mixtures of Kollidone VA64/Kollidone 90F and Kollidone VA64/Kollidone K17, respectively, at ratios of 10/90, 20/80, 30/70, 40/60, 50/50, 60/40, 70/30, 80/20, 90/10 (by weight) were prepared by weighing in appropriate amounts of the polymers and mixing in a ball mill at 50 Hz for 30 seconds.

DSC analyses were performed using a Mettler Toledo (Schwerzenbach, Switzerland) DSC 1 instrument controlled by STAR software version 9.10. Samples of the above mixtures and of the pure polymers weighing around 6 mg were measured in open aluminium pans. Thermograms were recorded between 20 and 220° C. (between 20 and 250° C. in a third run of VA64/90 F mixtures) at a rate of 10° C./min.

The Kollidone VA64/Kollidone 90F mixtures showed a well-pronounced two-phase character with two glass transition temperatures (see FIG. 1). The separate glass transition temperatures can be attributed to the individual polymers. This means that the melting of the polymers did not result in the blending of the polymers on a molecular level to obtain a homogeneous system that consists of one phase (as defined in thermodynamics). Heating up to 250° C. produced similar results.

When the proportion of Kollidone 90F in the mixture exceeded 50% by weight, the glass transition temperature Tg attributable to Kollidone VA64 increased from about 104° C. to about 110° C. (see FIG. 2). This indicates that a small amount of Kollidone 90F dissolved in the Kollidone VA64. On the other hand, the Tg attributable to Kollidone 90F was largely independent of the composition of the polymer mixture.

Figure 3:
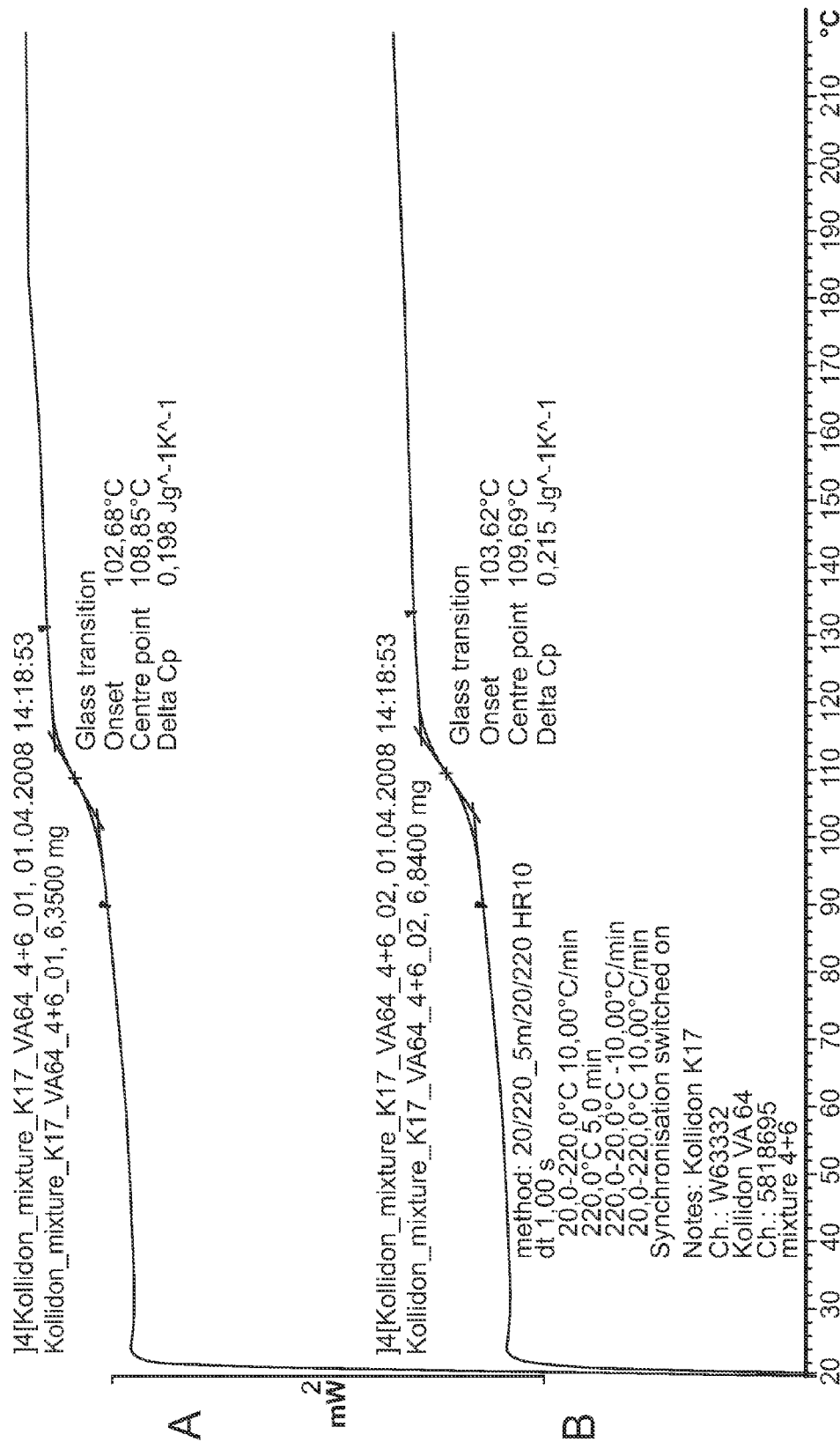
Figure 4:
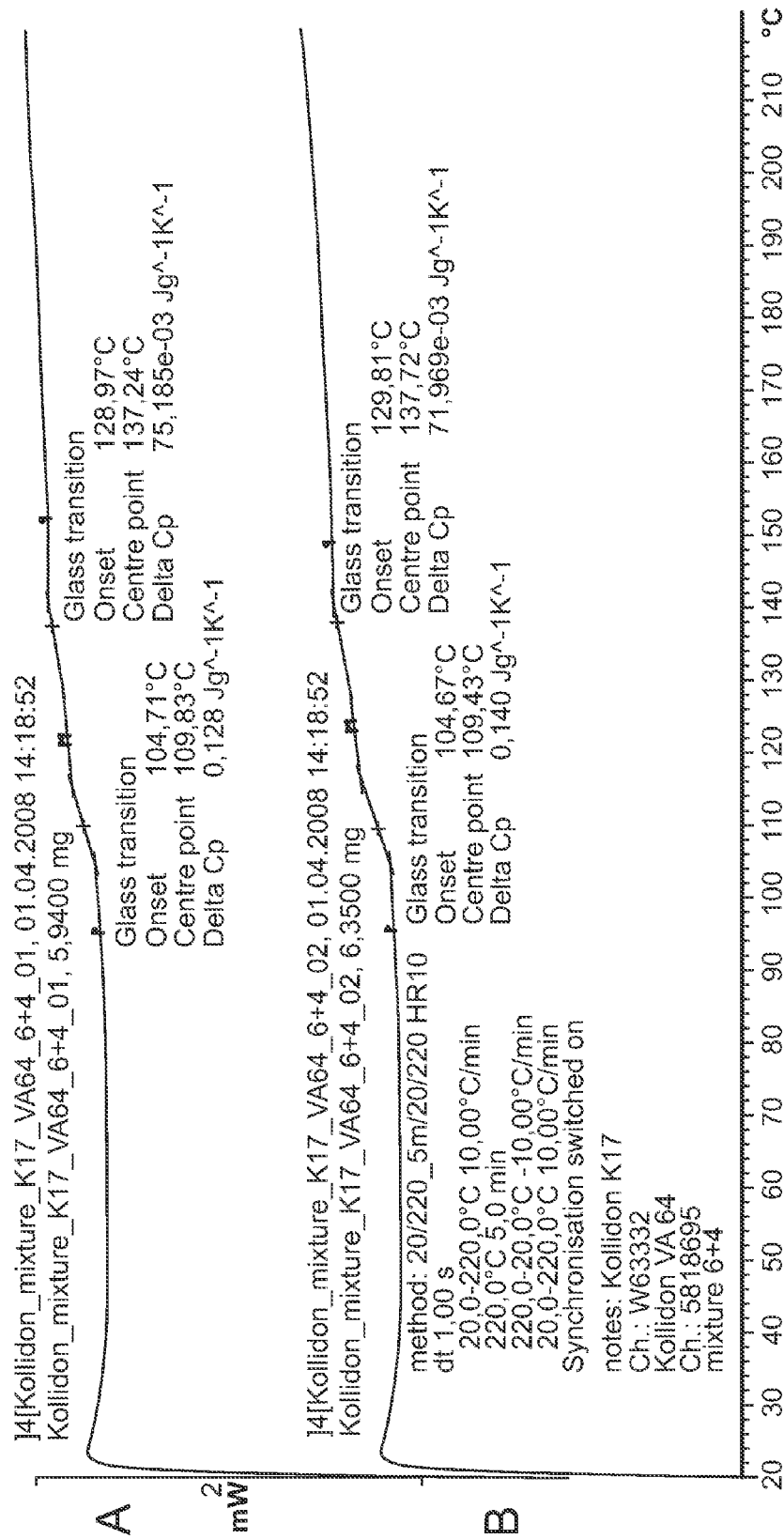

Mixtures of Kollidone VA64 and Kollidone K17 exhibited a single glass transition temperature, which takes an intermediate position between the corresponding glass transition temperatures of the individual polymers (see FIGS. 3, 5). In the mixtures containing 20%, 50%, and 60% by weight Kollidone K17, a small transition was observed, which could be attributed to Kollidone K17 (the thermogram of the 60/40 mixture Kollidone VA64/Kollidone K17 is shown in FIG. 4). However, the height of the transition attributable to Kollidone K17 was significantly lower than the height of the glass transition attributable to the polymer blend. Thus, it is considered that the occurrence of a second glass transition in these experiments was caused by inhomogeneities in the initial powder mixture.

What is claims is:

1. A pharmaceutical dosage form which comprises a solid dispersion product of at least one active ingredient dispersed in a polymeric carrier composition, the polymeric carrier composition comprising
    a) a vinylpyrrolidone homopolymer in which at least 95% by weight of the homopolymer has a molecular weight within the range of from 2,000 to 11,000; and
    b) a vinylpyrrolidone copolymer of vinylpyrrolidone and at least one vinylester having a weight-average molecular weight of from 10,000 to 80,000, wherein the weight ratio of a) to b) is in the range of from 5:95 to 50:50, wherein the at least one vinyl ester is vinylacetate.

2. The dosage form of claim 1, wherein the vinylpyrrolidone copolymer has a ratio Mw/Mn in the range of from 1.5 to 5.0.

3. The dosage form of claim 1, wherein the vinylpyrrolidone copolymer comprises from 20 to 80% by weight of vinylpyrrolidone units, relative to the total weight of the copolymer.

4. The dosage form of claim 1, wherein the vinylpyrrolidone homopolymer consists of PVP K12 or PVP K17 or a mixture of both.

5. The dosage form of claim 1, wherein the polymeric carrier composition exhibits a single Tg.

6. The dosage form of claim 1, wherein the active ingredient is molecularly dispersed in the polymeric carrier composition.

7. The dosage form of claim 1, wherein the solid dispersion product additionally comprises at least one additive selected from solubilizers, flow regulators, disintegrants, bulking agents and lubricants.

8. A method of preparing a solid dosage form of claim 1 which comprises:
   a) preparing a liquid mixture containing the at least one active ingredient, the polymeric carrier composition and at least one solvent, and
   b) removing the solvent(s) from the liquid mixture to obtain a solid dispersion product.

9. A method of preparing a solid dosage form of claim 1 which comprises:
   a) preparing a homogeneous melt of said at least one active ingredient and the polymeric carrier composition, and
   b) allowing the melt to solidify to obtain a solid dispersion product.

10. The method of claim 9, additionally comprising grinding said solid dispersion product and compressing said solid dispersion product into a tablet.

* * * * *